US006296755B1

United States Patent
Wang et al.

(10) Patent No.: US 6,296,755 B1
(45) Date of Patent: Oct. 2, 2001

(54) ELECTROCHEMICAL PROCESS FOR OLEFIN RECOVERY USING TRANSITION METAL DITHIOLENE COMPLEXES

(75) Inventors: Kun Wang, Washington; Edward Ira Stiefel, Bridgewater, both of NJ (US)

(73) Assignee: Exxon Research and Engineering Co., Annandale, NJ (US)

( * ) Notice: Subject to any disclaimer, the term of this patent is extended or adjusted under 35 U.S.C. 154(b) by 0 days.

(21) Appl. No.: 09/290,626

(22) Filed: Apr. 13, 1999

(51) Int. Cl.$^7$ ............................... B01D 17/06; C25B 1/00
(52) U.S. Cl. ............................................. 205/688; 205/338
(58) Field of Search ...................... 205/338, 688

(56) References Cited

U.S. PATENT DOCUMENTS

| | | | |
|---|---|---|---|
| 5,414,194 | * 5/1995 | Dubois et al. | 585/855 |
| 5,430,225 | 7/1995 | Dubois et al. | 585/855 |
| 5,935,755 | * 8/1999 | Kazmaier et al. | 430/120 |

OTHER PUBLICATIONS

Terry et al, "Electrochemically Modulated Complexation Process for Ethylene/Ethane Separation", AIChE Journal, Jul. 1997, vol. 43, No. 7, pp. 1709–1716.
Suzuki et al, "Electrochemistry, Stability, and Alkene Complexation Chemistry of...", Inorg. Chem. 1997, 36, pp. 136–140; *No Month Available.
Jemaa et al, "Combined Mass and Energy Balance Analysis of...", Chemical Engineering Science, vol. 47, No. 6, pp. 1469–1479, 1992; *No Month Available.

Jemaa et al, "Electrochemically Modulated Equilibrium Stage Processes", Chemical Engineering Science, vol. 46, No. 4, pp. 1017–1026, 1991; *No Month Available.
Davison et al, "Metal Complexes Derived From cis–1, 2–Dicyano–1,2–Ethylenedithiolate and ...", Inorganic Syntheses, pp. 8–27; *No Date Available.
Dubois et al., "Characterization and Reaction Studies of Dimeric Molybdenum(III) Complexes", J. Am. Chem. Soc. (1979), vol. 101, No. 18, pp. 5245–5252; *No Month Available.*
E1X97393768896, Terry et al. (Jul.1997).
XP–002144042, Chemical Abstracts vol. 126, No. 9, Suzuki (1997).
XP–002144043, Chemical Abstracts vol. 114, No. 16, Jemaa et al. (1991).
XP–002144044, Chemical Abstracts vol. 116, No. 22, Jemaa et al. (1992).

* cited by examiner

Primary Examiner—Edna Wong
(74) Attorney, Agent, or Firm—Linda M. Scuorzo

(57) ABSTRACT

A novel scheme for olefin recovery/separation based on the redox properties of metal dithiolene complexes is described. The complex, [1,2-bis(cyano)ethylene-1,2-dithiolato]nickel, [$Ni(S_2C_2(CN)_2)_2$], when generated electrochemically, binds olefin to form an adduct. The olefin is released when the olefin adduct is reduced electrochemically. The reduced form of the metal dithiolene complex can then be re-oxidized to complete the cycle. For olefins such as 1-hexene, propylene, and ethylene, fast olefin binding and release is observed when modulated electrochemically. Olefin binding/release rates are fast as compared to the electrochemistry experiment (second or sub-second time-scale).

11 Claims, 3 Drawing Sheets

ELECTROCHEMICAL PROCESS FOR OLEFIN RECOVERY USING TRANSITION METAL DITHIOLENE COMPLEXES

FIELD OF THE INVENTION

The present invention relates to a process for the selective recovery of olefins from multi-component olefin streams by electrochemically driven olefin complexation/dissociation.

BACKGROUND OF THE INVENTION

Separation of olefins is an important process in the chemical and petrochemical industry. Currently, the separation is usually done by cryogenic distillation. However, this technology is energy and capital intensive considering the large volume of olefins produced every year. As a result, alternative technologies have been actively sought.

Separation techniques that employ separating agents are attractive alternatives. Reversible olefin complexation in solution using metal ions such as $Cu^+$ and $Ag^+$ has been reported. However, these reactions are sensitive to common contaminants such as acetylene, carbon monoxide, and hydrogen sulfide, and the separation schemes use either temperature- or pressure-swing to release olefin.

Some literature reports describe removal and concentration of certain materials, e.g., contaminants, using electrochemically modulated schemes. Separation of ethylene using electrochemical schemes based on simple metal ions in aqueous solution has been reported. For example, a Cu(I)/Cu(II) chloride system has been reported (AICHE J. 1997, 43, 1709–1716) that can reversibly bind ethylene when modulated electrochemically. However, the binding affinity of Cu(I) to ethylene was small due to competitive complexation with chloride anion. In a subsequent report (Inorg. Chem., 1997, 36, 136–140), copper (I) trifluoromethanesulfonate (CuOTf) was used, where the weakly coordinating anion $OTf^-$ allows Cu(I) solution to more efficiently absorb ethylene. Process analyses for certain separation schemes based on electrochemically modulated complexation have appeared in the literature (Chem. Eng. Sci., 1991, 46, 1017–1026; Chem. Eng. Sci., 1992, 47, 1469–1479). The analyses indicate that an electrochemically modulated complexation process can have advantages over normal solvent extractions, as long as suitable complexing agents can be developed. However, an electrochemically driven scheme for olefin separation using transition metal complexes, especially transition metal dithiolene complexes, has not been reported.

An electrochemically driven process has advantages such as possible reduction in volume of the unit and better control of olefin binding and release rates. Moreover, the location and partial pressure of the olefin released can be controlled by specifying the position and electric potential of the electrodes.

Thus, it is highly desirable to develop improved reversible binding agents for use in processes for separating olefins from complex mixtures containing them.

None of the references regarding transition metal dithiolene complexes teaches or suggests that the dithiolene complexes can react with simple olefins (e.g., $C_2$ to $C_6$ olefins) reversibly under ambient conditions; or that such a process reversible binding of olefins can be controlled electrochemically. What is desired is an electrochemical process by which simple olefins reversibly bind to a compound or complexing agent using a transition metal dithiolene is selective to such simple olefins in multicomponent olefin streams and, desirably is also tolerant to contaminants and poisons typically present in olefin-containing streams.

Additionally, it would be desirable to have a process for recovering olefins, particularly simple olefins (e.g., $C_2$–$C_6$) from streams containing these simple olefins, as well as other hydrocarbons and contaminants in which the complexing agent reversibly binds the olefin to be recovered.

SUMMARY OF THE INVENTION

Figure 1:
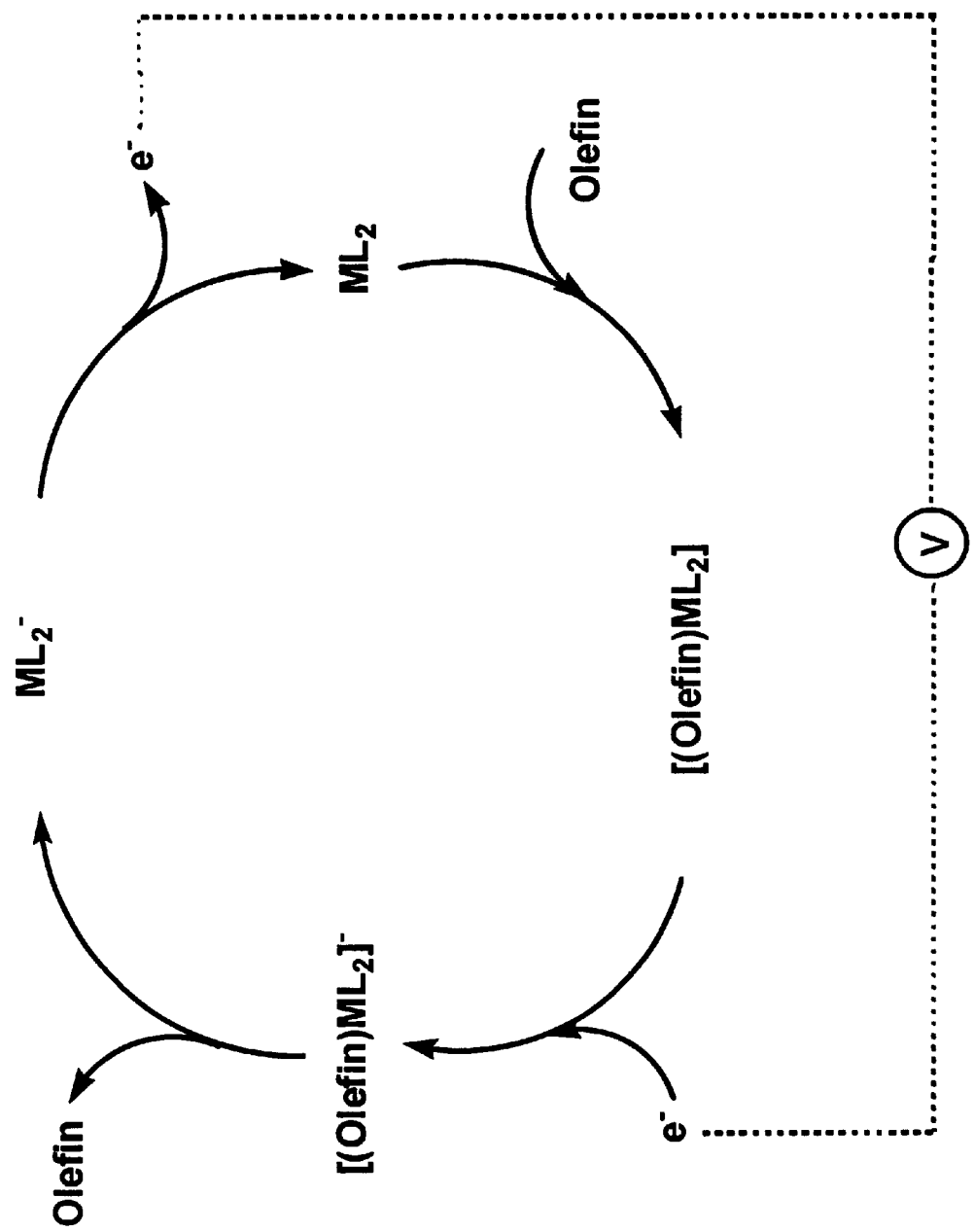
FIG. 1 is a simplified scheme of the electrochemical process.

The present invention relates to a method for electrochemically separating and/or recovering olefins, particularly simple olefins ($C_2$–$C_6$ olefins), from a stream containing the olefin and at least one other hydrocarbon by reversibly binding the olefin with a transition metal dithiolene complex.

The present invention may comprise, consist or consist essentially of the elements or steps disclosed herein and includes the products produced by the process disclosed herein.

DETAILED DESCRIPTION OF THE INVENTION

The present invention relates to an electrochemically-driven process for olefin recovery. Cyclic voltammetry reveals that metal dithiolene complexes can undergo multiple, reversible, one-electron redox reactions. Olefin binding may be sensitive to the electronic environment of the complexing reagent. Electrochemically oxidizing or reducing the dithiolene complex may therefore significantly affect its affinity to olefins and thereby can be used to control the binding and the release of the olefins.

Thus, the present invention provides a method for electrochemically separating and/or recovering olefins from streams containing olefins and other inorganic and hydrocarbonaceous components or contaminants by contacting the stream with a metal dithiolene complex to remove the olefins. Desirably, the olefins to be separated are low molecular weight, simple olefins, e.g., $C_2$–$C_6$, preferably $C_2$–$C_3$ olefins and, the process is selective for such olefins. The process is carried out by contacting a stream containing the olefins to be separated with an extracting or complexing agent that is a Group VIII metal bis(dithiolene) complex; where the binding and release of the olefins are achieved in an electrochemical cell by suitable change in the electric potential. Thus, the present invention is a process for electrochemically binding and release of simple olefins with transition metal dithiolene complexes in a selective and reversible manner; this has not been accomplished in the art.

Dithiolene is a commonly used name for 1,2-enedithiolate or benzene-1,2-dithiolate and related dithiolates. For simplicity, the term dithiolene is used when possible throughout the text.

The transition metal dithiolene complexes are selected from complexes represented by the formulas (I) $A_x\{M[S_2C_2(R^aR^b)]_2\}$ and (II) $A_x\{M[S_2C_6(R^1R^2R^3R^4)]_2\}$.

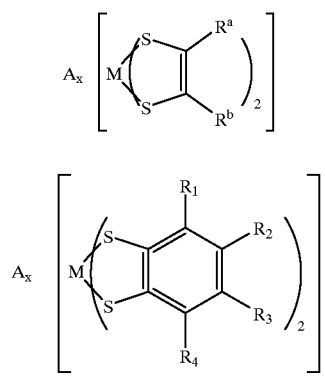

(I)

(II)

The structural formula for the transition metal dithiolene complex is shown above in Formula (I) for $A_x\{M[S_2C_2(R^aR^b)]_2\}$ and in Formula (II) for $A_x\{M[S_2C_6(R^1R^2R^3R^4)]_2\}$.

In formula (I), M is a transition metal, preferably a Group VIII metal, $R^a$ and $R^b$ may be the same or different, and are independently selected from hydrogen, electron-withdrawing groups including those that are or contain heterocyclic, cyano, carboxylate, carboxylic ester, keto, nitro, and sulfonyl groups, and hydrocarbyl groups, including alkyl, cyclo alkyl, alkenyl and aryl groups, unsubstituted or fully or partly substitued, preferably substituted with electron-withdrawing groups. Preferably the groups are cyano groups or halo substituted alkyl groups, more preferably the halo substituents on the carbon atoms are fluoro group. Most preferably $R^a$ and $R^b$ are $CF_3$ or CN.

As known in the art, another type of dithiolene complex that may also be used contains (substitued) benzene dithiolato ligands, represented by the structure in formula (II) above. In formula (II), M is also a transition metal, preferably a Group VIII metal, $R^1$, $R^2$, $R^3$, and $R^4$ are independently selected and may be the same or different, and $R^1$ to $R^4$ are hydrogen, electron-withdrawing groups as described above, and unsubstituted or fully or partly substituted hydrocarbyl groups including alkyl, cycloalkyl, alkenyl and aryl groups, preferably with substituents at the carbon atoms the hydrocarbyl group that are electron-withdrawing groups. Preferably, the group is a halo group.

Those skilled in the art would recognize more complex forms in the dithiolene class that also may be used.

In formulas (I) and (II), A may be any suitable cation, e.g., Group IA (e.g., Li, Na, K, Rb, Cs), Group IB (e.g., Ag, Cu), suitable onium ions of the formula $E(R_cR_dR_eR_f)$ wherein E is nitrogen, phosphorous, arsenic and $R_c-R_f$ may be the same or different, and are independently selected from hydrogen, alkyl and aryl groups, unsubstituted or substituted (including, but not limited to, fluorinated) having a chain length equal to or greater than $C_1$. The stoichimetry can be varied such that x=0, 1, 2.

For instance, generation of the anionic species from suitable starting materials may be carried out as known in the art (e.g., Holm et al, Inorg. Synth., 10, 8–26 (1967)). Similarly, generation of the neutral species (x=0) may also be carried out as known in the art.

The transition metals are preferably Fe, Co, Cu, Ni, Pd and Pt, more preferably Ni, Pd and Pt, most preferably Ni. Thus the complex can be any neutral or anionic form of metal bis(1,2-enedithiolate), preferably a group VIII metal bis(1,2-enedithiolate), more preferably substituted 1,2-enedithiolate with electron withdrawing groups as specified above, and most preferably the bis[1,2-bis(cyano)ethylene-1,2-dithiolato] metal monoanion.

Unexpectedly, Applicants have discovered that the transition metal dithiolene complexes described herein have the capacity to reversibly bind olefins, particularly simple olefins, desirably $C_2$–$C_6$ olefins, preferably $C_2$–$C_3$ olefins. If higher olefins are also to be separated and/or recovered, they subsequently may be separated from the simple olefins by known methods such as distillation. Typically, but not necessarily olefin containing non-interfering streams are primarily hydrocarbon containing streams. However, they also may contain inorganic components.

The process is carried out by contacting an olefin-containing hydrocarbon stream with a transition metal dithiolene complex of the formula $A_x\{M[S_2C_2(R^aR^b)]_2\}$ and M, $R^a$, $R^b$ are as specified above or of the formula $A_x\{M[S_2C_6(R^1R^2R^3R^4)]_2\}$ wherein M, $R^1$, $R^2$, $R^3$, and $R^4$ are as specified above. All or part of the process may be carried out in an electrochemical cell. The streams may be liquid, gaseous, or mixed. The solvent should be a suitable solvent to provide electrical conductivity within the cell, e.g., a polar organic liquid, an ionic liquid, or an aqueous solution provided that it is essentially non-interfering with the reaction of the olefin and metal dithiolene complex. For gaseous olefins, a saturated solution was used. Concentrations of liquid olefins are normally at the molar level. Olefin separation is accomplished by contacting the stream containing the olefin to be separated with the metal dithiolene complex in an electrochemical cell at a specific potential such that the complex is in the oxidized (e.g., neutral) form which forms an adduct with the olefin to be separated; olefin recovery is accomplished by reducing the adduct at lower potential so as to release the olefin and regenerate the reduced form of the dithiolene complex. Depending on the nature of the complex used, the potential range can be within, for example, –2 to 2 volts although the actual potential variation may be as small as 0.5 volt or less.

As stated previously, the olefin-containing stream also may contain any number of other components or contaminants of the primarily hydrocarbonaceous stream in addition to the simple olefins, e.g., alkanes, aromatics, $H_2$, CO, $H_2S$, $H_2O$, and alkynes such as acetylene. The process of the present invention is selective and reversible electrochemically with respect to the olefins, and the dithiolene complexes are able to withstand the presence of other contaminants, especially at the level usually found in typical refinery or chemical streams (typically less than about 10 wt %).

Thus, altering the oxidation state of the Group VIII metal dithiolene complexes to achieve binding and then release of the olefins to be separated or recovered is accomplished in the redox system. Ultimately, the olefin must be dissociated from the complex if the metal dithiolene complex is to be recovered and recycled or reused. In addition to the electric potential switch, other process conditions may be selected or manipulated to facilitate the reversibility of the olefin binding to the metal dithiolene complex, and the subsequent release of the olefin and recovery of the metal dithiolene. Thus, for example, a change in temperature (e.g., increase to release olefin), or pressure (e.g., decrease to release olefin), or solvent (e.g., a polar solvent to facilitate the reaction) may be employed in combination with the electric potential switch to achieve reversibility of olefin binding.

Advantage can be taken of the oxidation state of the metal in the metal dithiolene complexes with the use of redox systems (e.g., an electrochemical cell) in which the oxidized form of the metal dithiolene complex binds the olefin to form an olefin-metal dithiolene adduct, whereupon application of a relatively negative potential the reduced (i.e., electron rich) metal dithiolene complex releases the olefin and the regeneration of the starting metal dithiolene. Depending on the nature of the complex used, the potential range can be within, for example, −2 to 2 volts although the actual potential variation may be as small as 0.5 volt or less. The process may be represented in a simplified manner is specified in FIG. 1. The cation A is omitted from the scheme. In FIG. 1, M is a transition metal as defined in Formula I and II, L is a dithiolene ligand as defined above. The cycle can start from either $ML_2^-$ or $ML_2$.

Desirably, conditions for separation of the olefin from the adduct to metal dithiolene complexes should be selected to facilitate recovery of the metal dithiolene complexes for use in subsequent cycles.

Thus in the present invention olefin binding occurs once the neutral form is generated by electrochemical oxidation. Thus, for example, $[Ni(S_2C_2(CN)_2)_2]$ binds olefins in its neutral form. However, it does not bind olefins in its reduced forms. When the olefin-metal dithiolene adduct is reduced electrochemically, affinity of the metal dithiolene complex to olefin is decreased and the olefin is released The reduced form of the metal dithiolene complex can then be re-oxidized for use in the subsequent cycle.

Applicants have, using cyclic voltammetry, demonstrated the electrochemically-driven, reversible reactions of $[Ni(S_2C_2(CN)_2)_2]$ with olefins such as 1-hexene, propylene, and ethylene. In such cases, fast olefin binding occurs once the neutral form is generated electrochemically and the olefin is quickly released upon electrochemical reduction of the olefin metal dithiolene adduct. Olefin binding and release rates are on the time-scale of seconds or less.

Suitable electrochemical cells are known to those skilled in the art for the electrochemical processes (e.g., Danly, D. E. "Emerging Opportunities for Electroorganic Processes. A Critical Evaluation of Plant Design and Economics" Marcel Dekker, 1984).

Advantageously, the process of the present invention may be used to enhance the recovery (yield) of simple olefins from multi-component olefin streams containing hydrocarbonaceous and non-hydrocarbonaceous contaminants.

EXAMPLES

Example 1

General experimental procedure for electrochemically-driven olefin binding: $(Bu_4N)Ni[S_2C_2(CN)_2]_2$ and $(Bu_4N)_2Ni[S_2C_2(CN)_2]_2$ were prepared following the literature methods (Inorg. Synth., Vol. 10, 8–26, (1967)). Cyclic voltammetry was carried out using a BAS100A Electrochemical Analyzer. A three-electrode cell was used in which a Pt-disk working electrode, a Pt-wire auxiliary electrode, and a $Ag^+$/Ag-wire reference electrode were employed. Experiments were carried out in $CH_2Cl_2$ with $Bu_4NPF_6$ as supporting electrolyte. The ferrocene/ferrocenium (Fc/Fc$^+$) couple was used as standard for potential calibration.

Example 2

Figure 2:
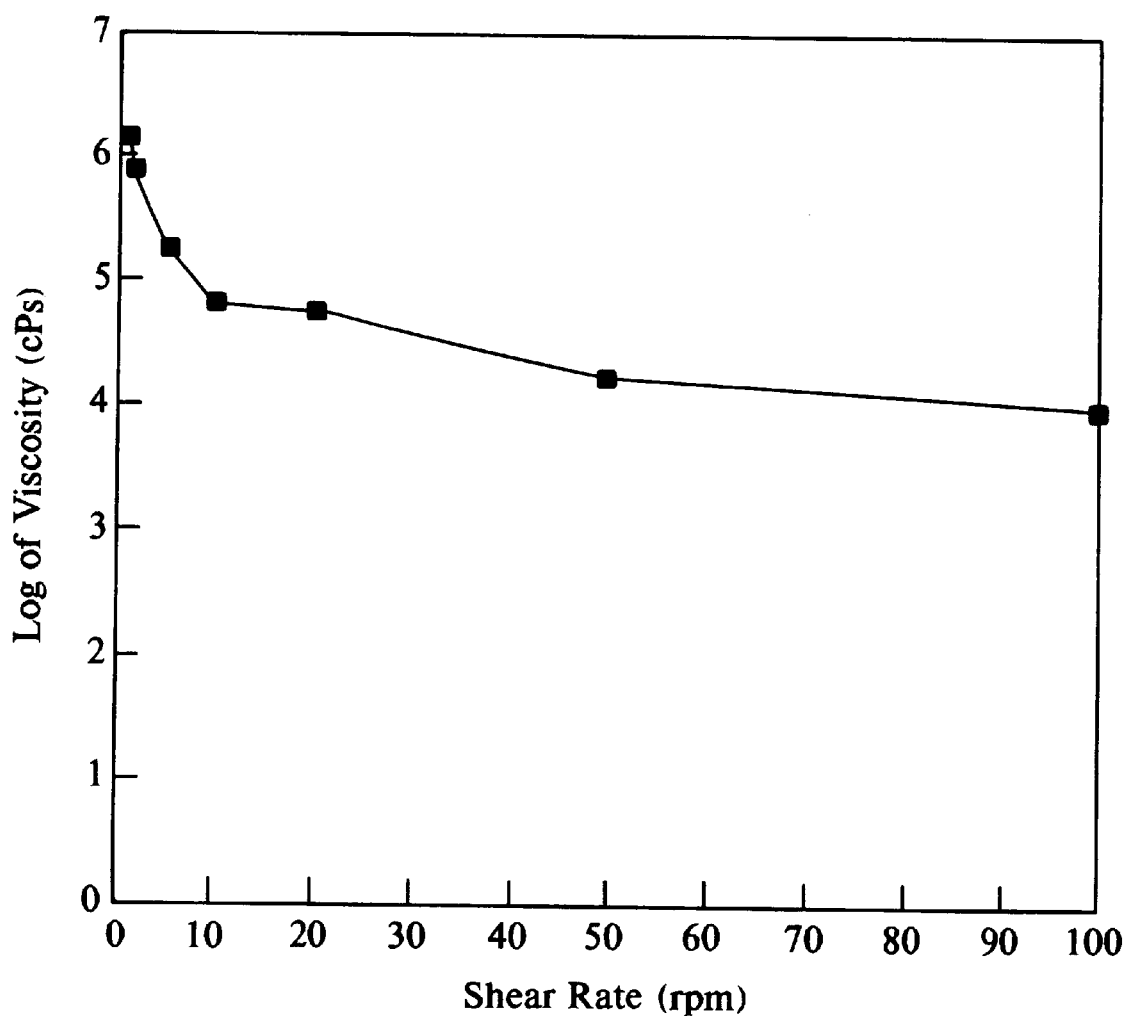
FIG. 2 is a cyclic voltammogram of $(Bu_4N)Ni[S_2C_2(CN)_2]_2$ (2 mM in $CH_2Cl_2$, scan rate=100 mV/s) showing two reversible couples.
Figure 3:
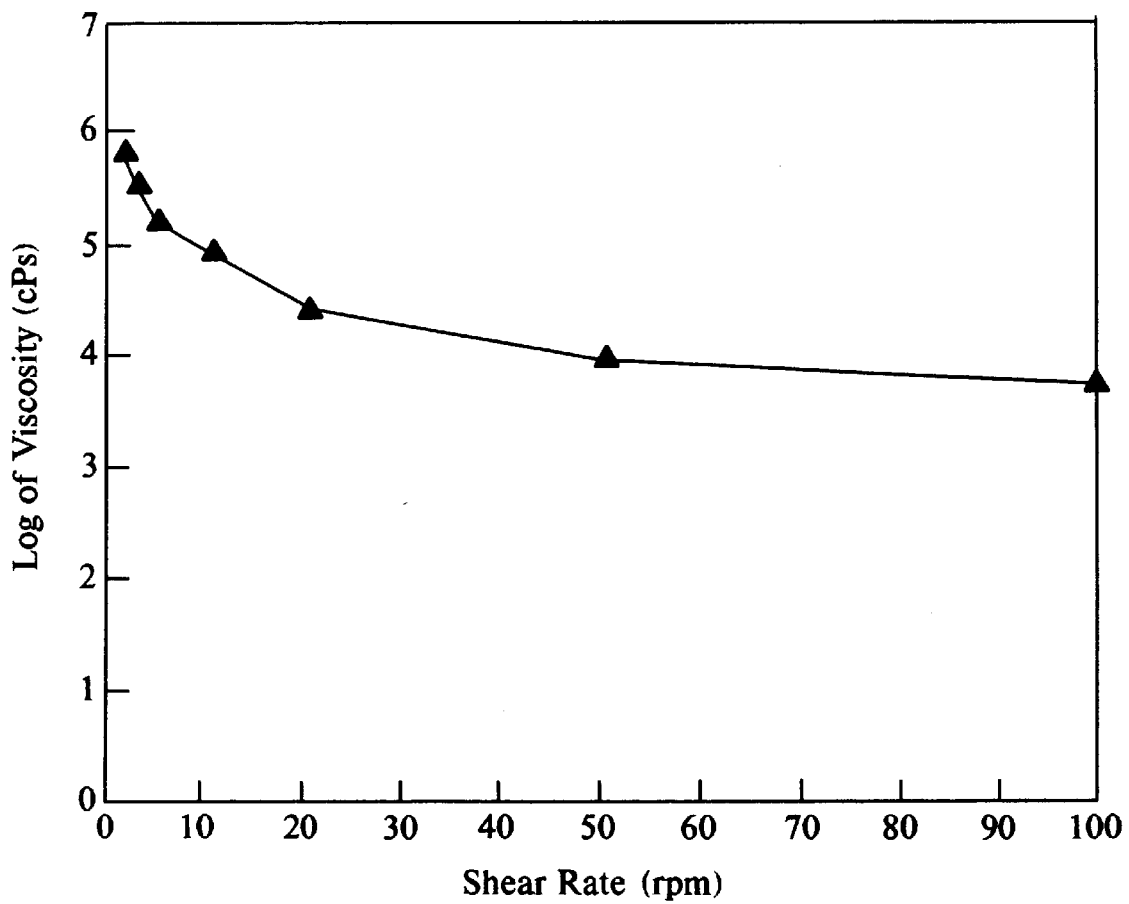
FIG. 3 is a cyclic voltammogram of $(Bu_4N)Ni[S_2C_2(CN)_2]_2$ (2 mM in $CH_2Cl_2$, scan rate=100 mV/s) in the presence of 1-hexene (0.1 M).
Figure 2:
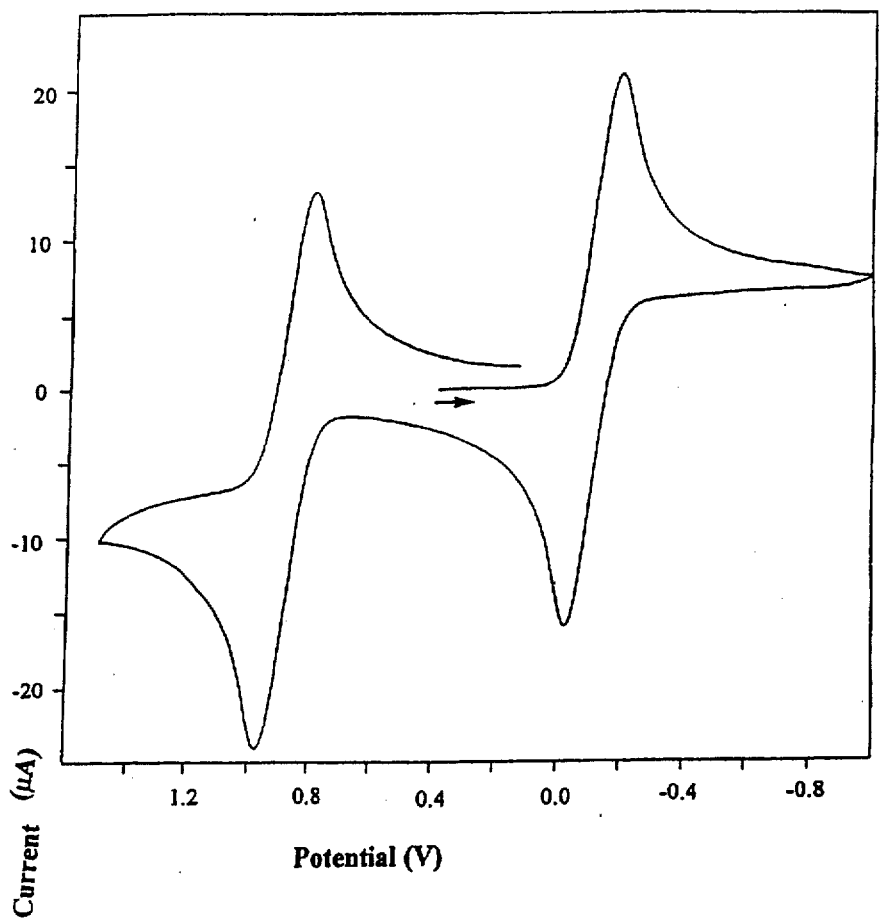
Figure 3:
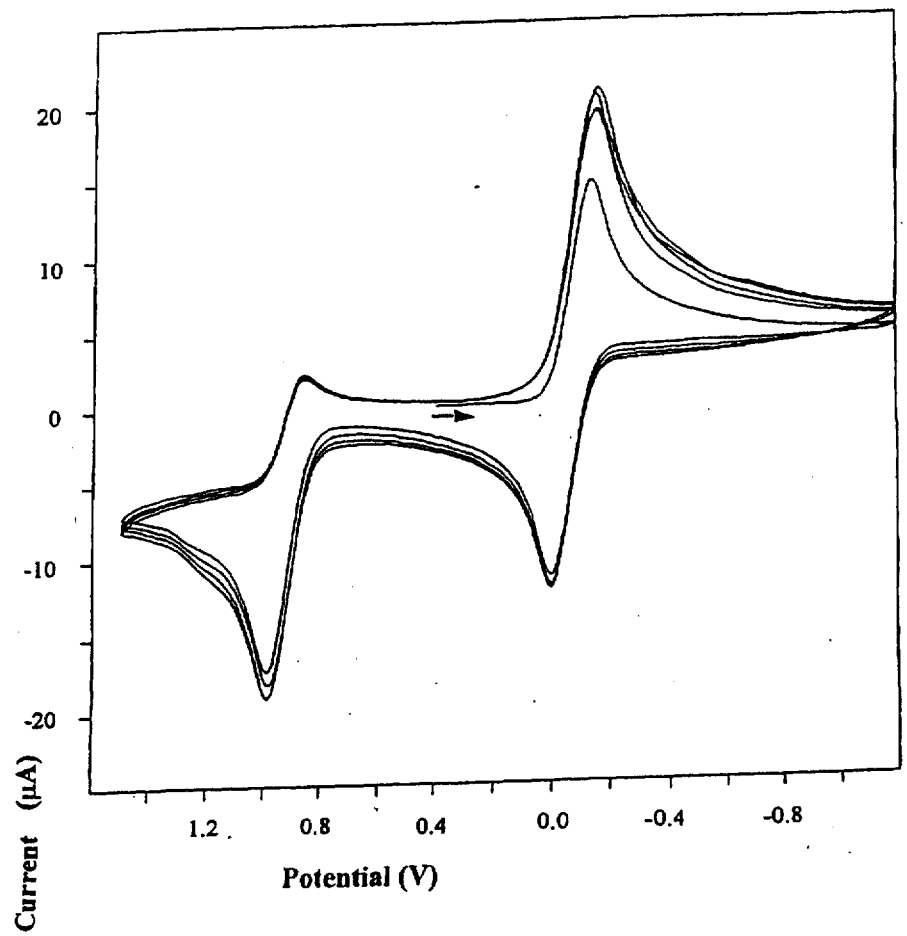

Cyclic voltammetry of $(Bu_4N)Ni[S_2C_2(CN)_2]_2$ in the presence of 1-hexene: In an electrochemical cell, 11 mg of $(Bu_4N)Ni[S_2C_2(CN)_2]_2$ ($[Ni(mnt)_2]^-$, 0.02 mmol. mnt=$S_2C_2(CN)_2$) was dissolved in 10 mL of 0.1 M $Bu_4NPF_6$ solution in dry, degassed $CH_2Cl_2$. The solution was scanned at rates of 100, 400, and 1000 mv/s. Two reversible waves were observed at all three rates as shown in FIG. 2. 125 μL of 1-hexene (1.0 mmol) was quickly added to the solution with stirring; and the solution was scanned again at different scan rates. The $[Ni(mnt)_2]^-/[Ni(mnt)_2]^{2-}$ couple was virtually unaffected in the initial scan. However, for the $[Ni(mnt)_2/[Ni(mnt)_2]^-$ couple, the cathode current $i_c$ decreases significantly as compared to the anode current $i_a$ ($i_c/i_a$=0.43) in the presence of excess 1-hexene. This observation reveals that some percentage of $[Ni(mnt)_2]$, once formed, has reacted with 1-hexene thereby reducing the concentration of "free" $[Ni(mnt)_2]$. There is no significant change in the $i_c/i_a$ ratio when the scan rate is varied (100, 400, and 1000 mv/s). These facts indicate that there is reaction between $[Ni(mnt)_2]$ and 1-hexene; and that the reaction is faster than, or at least comparable to, the electrochemical time-scale (seconds or sub-second). The fact that $i_c/i_a$ is not zero suggests that the reaction is an equilibrium. Otherwise, a complete reaction in the presence of large excess 1-hexene will result in zero or close to zero cathode current ($i_c$). Scanning to more negative potential (reducing the 1-hexene adduct) reveals that the $[Ni(mnt)_2]^-/[Ni(mnt)_2]^{2-}$ couple is only slightly affected (but is still reversible), which reveals that the adduct quickly releases 1-hexene when reduced. The fact that the $[Ni(mnt)_2]^-/[Ni(mnt)_2]^{2-}$ couple deformed slightly on further scanning suggests that the olefin adduct has similar redox potential to that of $[Ni(mnt)_2]^-$ (for the $[Ni(mnt)_2]^-/[Ni(mnt)_2]^{2-}$ couple). Multiple scans and scanning at different rates did not reveal any significant changes in the shape of either wave indicating that a fast, clean equilibrium reaction occurred between 1-hexene and $[Ni(mnt)_2]$. Clearly, as shown in FIG. 3 fast olefin binding and release can be achieved and modulated electrochemically.

Example 3

Cyclic voltammetry of $(Bu_4N)Ni[S_2C_2(CN)_2]_2$ in the presence of ethylene: A similar procedure to that in Example 2 was followed except that ethylene was passed through the solution of $Ni(mnt)2]^-$ for 90 seconds to make a saturated solution of ethylene. The $i_c/i_a$ ratio of the $[Ni(mnt)_2]/[Ni(mnt)_2]^-$ couple decreased from ca. 1 to 0.6 in the presence of ethylene, while that of the $[Ni(mnt)_2]^-/[Ni(mnt)_2]^{2-}$ couple is virtually unaffected. It is indicated that a fast reaction with ethylene occurs (to form adducts) when $[Ni(mnt)_2]$ is generated electrochemically; and the adduct quickly releases olefin when reduced. The equilibrium reaction appears to be fast and clean.

Example 4

Cyclic voltammetry of $(Bu_4N)Ni[S_2C_2(CN)_2]_2$ in the presence of propylene: Example 3 was repeated for propylene. Similar results were observed. In the presence of excess propylene, $i_c/i_a$ for the $[Ni(mnt)2]/[Ni(mnt)_2]^-$ couple dropped from ca. 1 to 0.26, while that of the $[Ni(mnt)_2]^-/[Ni(mnt)_2]_{2-}$ couple did not change. It is indicated that a fast reaction with propylene occurs (to form adducts) when $[Ni(mnt)_2]$ is generated electrochemically; and the adduct quickly releases olefin when reduced. The equilibrium reaction appears to be fast and clean.

What is claimed is:

1. An electrochemical method for separating olefins from olefin-containing streams, comprising: in an electrochemical cell contacting an olefin containing stream with a metal dithiolene compound selected from compounds represented by the formulas $A_x\{M[S_2C_2(R^aR^b)]_2\}$ or $A_x\{M[S_2C_6(R^1R^2R^3R^4)]_2\}$ at an electric potential sufficient to generate an oxidized form that binds the olefin to form an adduct of the olefin with the metal dithiolene compound and reducing the adduct at a lower electric potential sufficient to release the olefin, wherein A is a cation selected from Group IA, IB or onium ions, and X is 0, 1 or 2. M is a transition metal, $R^a$ and $R^b$ and $R^1$, $R^2$, $R^3$, and $R^4$ are independently selected and may be the same or different and are selected from hydrogen, electron withdrawing groups selected from halo-, heterocyclo-, cyano-, carboxylate, carboxylic ester, keto, nitro or sulfonyl groups, or trifluoromethyl or substituted or unsubstituted hydrocarbyl groups.

2. The process of claim 1 wherein the olefin-containing stream contains at least one of paraffins, $H_2$, CO, $C_2H_2$, $H_2S$, $H_2O$, $CO_2$, or alkynes.

3. The process of claim 1 further comprising releasing the olefin from the adduct to recover the olefin by applying suitable electric potential.

4. The process of claim 3 wherein binding and releasing the olefin is carried out by effective change in electric potential in combination with changing at least one of temperature, pressure, or solvent.

5. The process of claim 1 wherein contacting is carried out at a temperature of from about −60° C. to 150° C.

6. The process of claim 1 wherein $R^a$, $R^b$, $R^1$, $R^2$, $R^3$, and $R^4$ are independently selected from $CF_3$ or CN.

7. The process of claim 1 wherein M is selected from Ni, Pd or Pt.

8. The process of claim 1 further comprising the step of recovering the metal dithiolene compound from the olefin-containing stream.

9. The process of claim 1 wherein the electric potential is from −2 to 2V.

10. The process of claim 1 wherein the onium ion has the formula $E(R_c R_d R_e R_f)$ wherein E is selected from nitrogen or phosphorous, or arsenic and $R_c$–$R_f$ may be the same or different and are independently selected from hydrogen, aryl, or alkyl groups having a chain length equal to or greater than $C_1$.

11. The process of claim 1 wherein the olefins are $C_2$–$C_6$ olefins.

* * * * *

UNITED STATES PATENT AND TRADEMARK OFFICE
CERTIFICATE OF CORRECTION

PATENT NO. : 6,296,755 B1  
DATED : October 2, 2001  
INVENTOR(S) : Kun Wang et al.

It is certified that error appears in the above-identified patent and that said Letters Patent is hereby corrected as shown below:

Drawings,  
Please delete Figure 2 and 3 in the above issued patent. Please replace with the correct Figures 2 and 3 attached.

Signed and Sealed this

Twenty-eighth Day of May, 2002

*Attest:*

JAMES E. ROGAN  
*Director of the United States Patent and Trademark Office*

*Attesting Officer*